(12) United States Patent
Lincoln et al.

(10) Patent No.: US 6,709,420 B1
(45) Date of Patent: Mar. 23, 2004

(54) SWITCH-STYLE DRAIN ASSEMBLY FOR URINE COLLECTION CONTAINER

(75) Inventors: Brian Lincoln, Snellville, GA (US); Dan Nevill, Conyers, GA (US); Ken Butcher, Conyers, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/357,728

(22) Filed: Jul. 21, 1999

(51) Int. Cl.[7] .................................................. A61M 1/00
(52) U.S. Cl. ........................... 604/323; 604/317; 251/9; 251/97
(58) Field of Search ................................ 604/317, 320, 604/323, 327, 335, 349, 350; 600/573, 574; 222/107, 566; 383/107, 906; 251/9, 297

(56) References Cited

U.S. PATENT DOCUMENTS

| 4,272,051 | A | | 6/1981 | Huggins | |
|---|---|---|---|---|---|
| 4,305,403 | A | | 12/1981 | Dunn | |
| 4,540,156 | A | * | 9/1985 | Cross | 251/309 |
| 4,660,802 | A | | 4/1987 | Oscarsson | |
| 4,697,785 | A | | 10/1987 | Tuseth | |
| 4,702,740 | A | | 10/1987 | Bates | |
| 4,846,816 | A | * | 7/1989 | Manfredi | 604/323 |
| 4,955,879 | A | * | 9/1990 | Mervine | 604/327 |
| 5,032,118 | A | * | 7/1991 | Mason | 604/349 |
| 5,078,699 | A | | 1/1992 | Haber et al. | |
| 5,084,035 | A | | 1/1992 | Salvadori et al. | |
| 5,211,642 | A | * | 5/1993 | Clendenning | 604/410 |
| 5,226,564 | A | * | 7/1993 | Steer et al. | 604/317 |
| 5,318,550 | A | * | 6/1994 | Cermak et al. | 604/349 |
| 5,437,836 | A | * | 8/1995 | Yamada | 604/317 |
| 5,496,010 | A | * | 3/1996 | Collyer | 251/78 |
| 5,569,225 | A | * | 10/1996 | Fleury | 604/323 |
| 5,616,138 | A | * | 4/1997 | Propp | 604/317 |
| 5,618,277 | A | * | 4/1997 | Goulter | 604/349 |
| 6,261,254 | B1 | * | 7/2001 | Baron et al. | 604/323 |

FOREIGN PATENT DOCUMENTS

| DE | 93 13 842 U | 11/1993 |
|---|---|---|
| EP | 0 427 495 | 5/1991 |
| EP | 0 860 154 | 8/1998 |

* cited by examiner

*Primary Examiner*—Weilun Lo
*Assistant Examiner*—Michele Kidwell
(74) *Attorney, Agent, or Firm*—Kilpatrick Stockton LLP

(57) ABSTRACT

A drain assembly for a fluid collection container includes a housing attached to the container and defining a cavity therewithin. A stop is located within the cavity and is fixed relative to the housing. A switch having a closure member formed thereon is mounted within the cavity for rotary movement relative to the housing. In a disclosed embodiment the switch has a tab extending through the housing to facilitate rotation of the switch from outside the housing. A flexible, resilient tube in fluid communication with the interior of the fluid collection container has a portion disposed within the cavity and extending between the stop and the closure member of the switch. The tube is configured so that fluid discharged from the lower end of the tube is discharged through an opening in a lower portion of the housing. When the switch is rotated in one direction, the tube is compressed between the stop and the closure member, thereby preventing fluid flow through the tube. When the switch is rotated in the opposite direction, the closure member rotates away from the stop so as to permit the tube to open, thereby permitting fluid flow to be discharged from the fluid collection container through the tube.

33 Claims, 4 Drawing Sheets

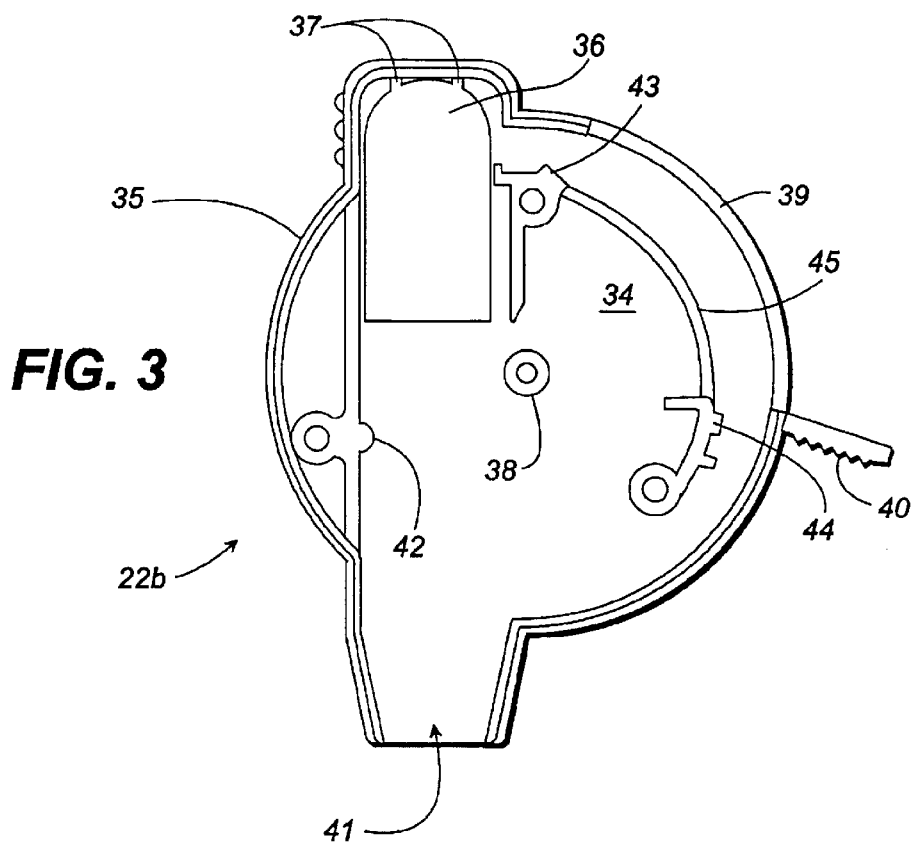
FIG. 3
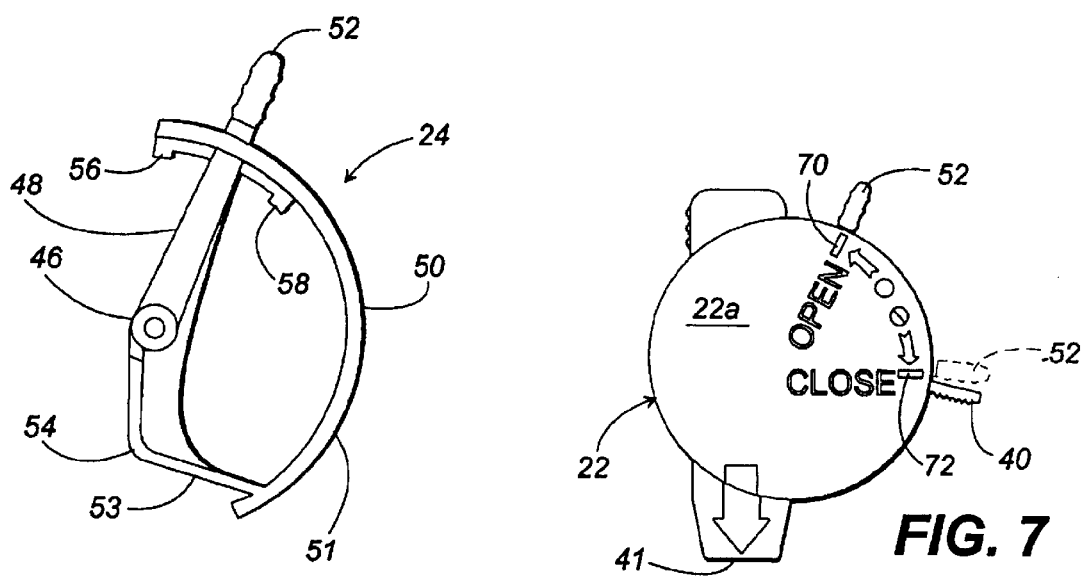
FIG. 4
FIG. 7

SWITCH-STYLE DRAIN ASSEMBLY FOR URINE COLLECTION CONTAINER

TECHNICAL FIELD

The present invention relates generally to urine collection containers and relates more specifically to a drain assembly for discharging the contents of a urine collection container.

BACKGROUND OF THE INVENTION

Urine collection bags are well known. Such collection bags receive and store urine from a catheter. When the bag becomes full, it is emptied through an outlet provided on the bag. The outlet can also be used to collect a urine sample for analysis.

A problem for healthcare personnel emptying the bag or collecting a urine sample through the outlet concerns operating the device without accidentally splashing urine on themselves during the operation of the outlet. Typically the operator will be holding the specimen container with one hand while trying to operate the outlet with the other. Operation of some outlets with one hand can be problematic. In addition, operation of some outlets may cause the discharge stream to be momentarily misdirected during operation of the outlet.

Thus there is a need for an outlet which can be operated reliably with only one hand and which provides control over the direction in which fluid is discharged. Preferably such an outlet should also be intuitive to operate.

There is a further need for an outlet tube device which can be operated without the fingers and hands of the operator being in the proximity of the discharge tube so as to minimize or eliminate the possibility of transferring bacteria, fungus, or other contaminant from the operator's hands to the tube, where the contaminant could find its way into the bag and hence to the patient, or from the tube to the operator's hands, causing an unsanitary situation and exposing the operator to the possibility of infection or disease.

Another problem for healthcare personnel emptying the bag or collecting a urine sample through the outlet concerns the possibility protective gloves being pinched or torn by the outlet tube mechanism. Once the integrity of the protective glove is compromised, the operator is exposed to the possibility of infection or disease. Thus there is a need for an outlet tube device which can be operated without the operator's protective gloves being pinched or torn by the outlet tube mechanism.

SUMMARY OF THE INVENTION

Stated generally, the present invention comprises an improved drain assembly for urine collection containers which satisfies all of the foregoing needs. The drain assembly can easily and reliably be operated with only one hand and is intuitive for a user to operate. It further provides the operator with control over the direction in which fluid is discharged, especially during opening and closing of the drain assembly. It can also be operated without the fingers and hands of the operator being in the proximity of the discharge tube. Thus the possibility is minimized or eliminated of transferring bacteria, fungus, or other contaminant from the operator's hands to the tube, where the contaminant could find its way into the bag and hence to the patient. The possibility is further minimized or eliminated of transferring contaminants from the tube to the operator's hands, where the contaminant could cause an unsanitary situation and expose the operator to the possibility of infection or disease. The outlet tube device of the disclosed embodiment can further be operated without the operator's protective gloves being pinched or torn by the outlet tube mechanism.

Stated somewhat more specifically, the present invention relates to a drain assembly for a fluid collection container. First and second housing portions are mounted to one another in fixed relation to form a housing. The housing is attached to a fluid collection container and defines a cavity therewithin. A stop is located within the cavity and is fixed relative to the housing. A switch is mounted within the cavity for rotary movement relative to the housing. The switch has a closure member formed thereon. In a preferred embodiment the switch has a tab extending through the housing to facilitate rotation of the switch from outside the housing. A flexible, resilient tube in fluid communication with the interior of the fluid collection container has a portion disposed within the cavity and extending between the stop and the closure member of the switch. The tube is configured so that fluid discharged from the lower end of the tube is discharged through an opening in a lower portion of the housing. In the disclosed embodiment the end of the tube is recessed well within the housing to prevent accidental contact between the operator and the discharge end of the tube. When the switch is rotated in one direction, the tube is compressed between the stop and the closure member, thereby preventing fluid flow through the tube. In the disclosed embodiment, rotating the switch to the "closed" position rotates a shield into position which closes the opening in the lower end of the housing. When the switch is rotated in the opposite direction, the closure member rotates away from the stop so as to permit the tube to open, thereby permitting fluid flow to be discharged from the fluid collection container through the tube.

Thus it is an object of the present invention to provide an improved drain assembly for urine collection containers.

It is another object of the present invention to provide a drain assembly for urine collection containers which can easily and reliably be operated with only one hand.

Still another object of the present invention is to provide a drain assembly for urine collection containers which provides the operator with control over the direction in which fluid is discharged, especially during opening and closing of the drain assembly.

Another object of the present invention is to provide a drain assembly for urine collection containers which is intuitive to operate.

Still another object of the present invention is to provide an outlet tube device which can be operated without the fingers and hands of the operator being in the proximity of the discharge tube so as to minimize or eliminate the possibility of transferring bacteria, fungus, or other contaminant from the operator's hands to the tube, where the contaminant could find its way into the bag and hence to the patient, or from the tube to the operator's hands, causing an unsanitary situation and exposing the operator to the possibility of infection or disease.

Other objects, features, and advantages of the present invention will become apparent upon reading the following specification, when taken in conjunction with the drawings and the appended claims.

BRIEF DESCRIPTION OF THE DRAWINGS

FIG. 3 is a front view of the back housing of the drain assembly of FIG. 2.

FIG. 4 is a front view of the valve member of the drain assembly of FIG. 2.

FIG. 7 is a front view of the drain assembly of FIG. 2.

DETAILED DESCRIPTION OF THE DISCLOSED EMBODIMENT

Figure 1:
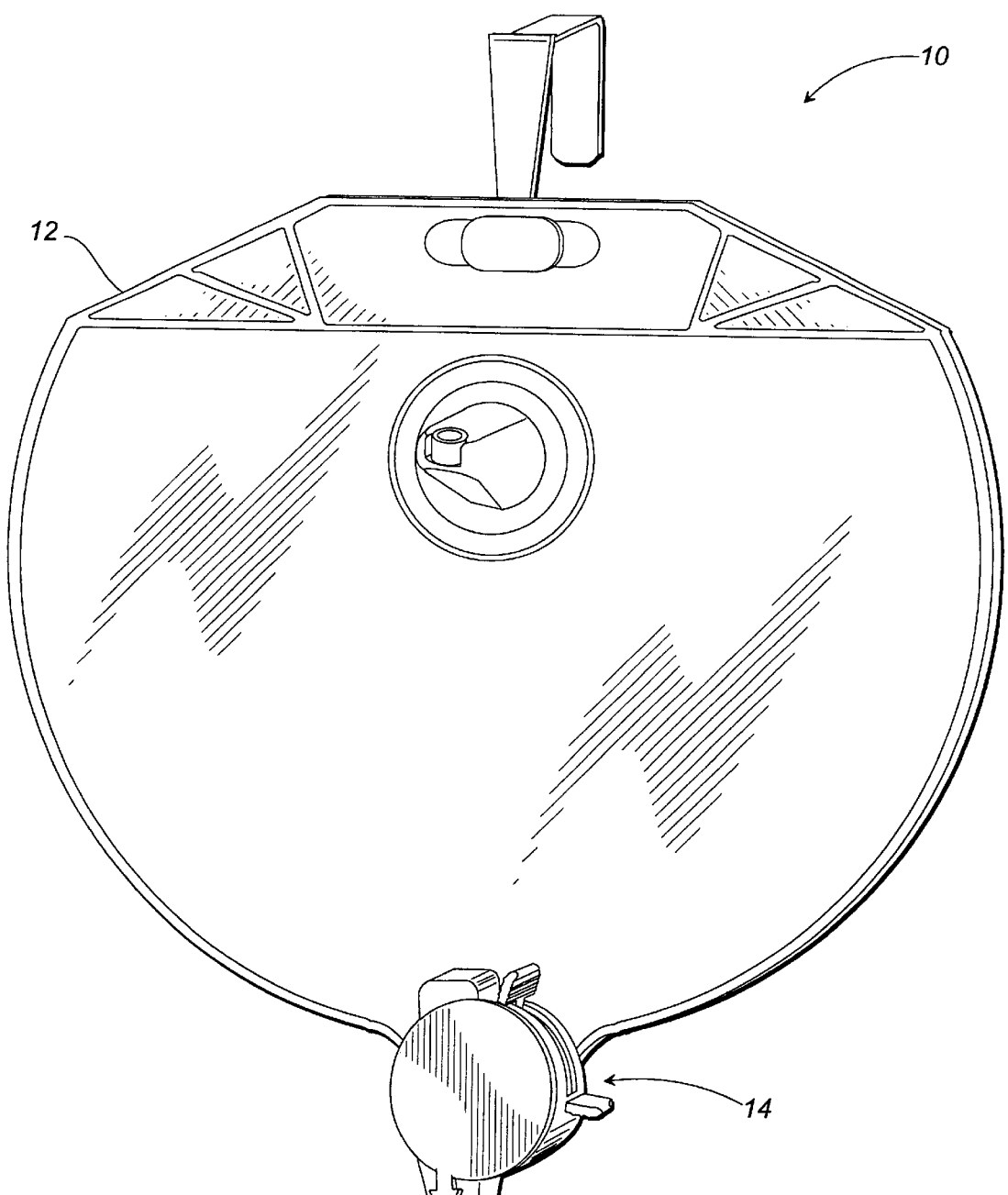
FIG. 1 is a front view of a urine collection container with switch-style drain assembly according to the present invention.

Referring now to the drawings, in which like numerals indicate like elements throughout the several views, FIG. 1 shows a urine collection container 10, including a collection bag 12 and drain assembly 14. The bag 12 is of conventional design and consists of mutually imposed, front and back sheets of a flexible, impermeable plastic such as polyvinyl chloride, heat welded around their peripheries to form a central collection chamber therebetween.

Figure 2:
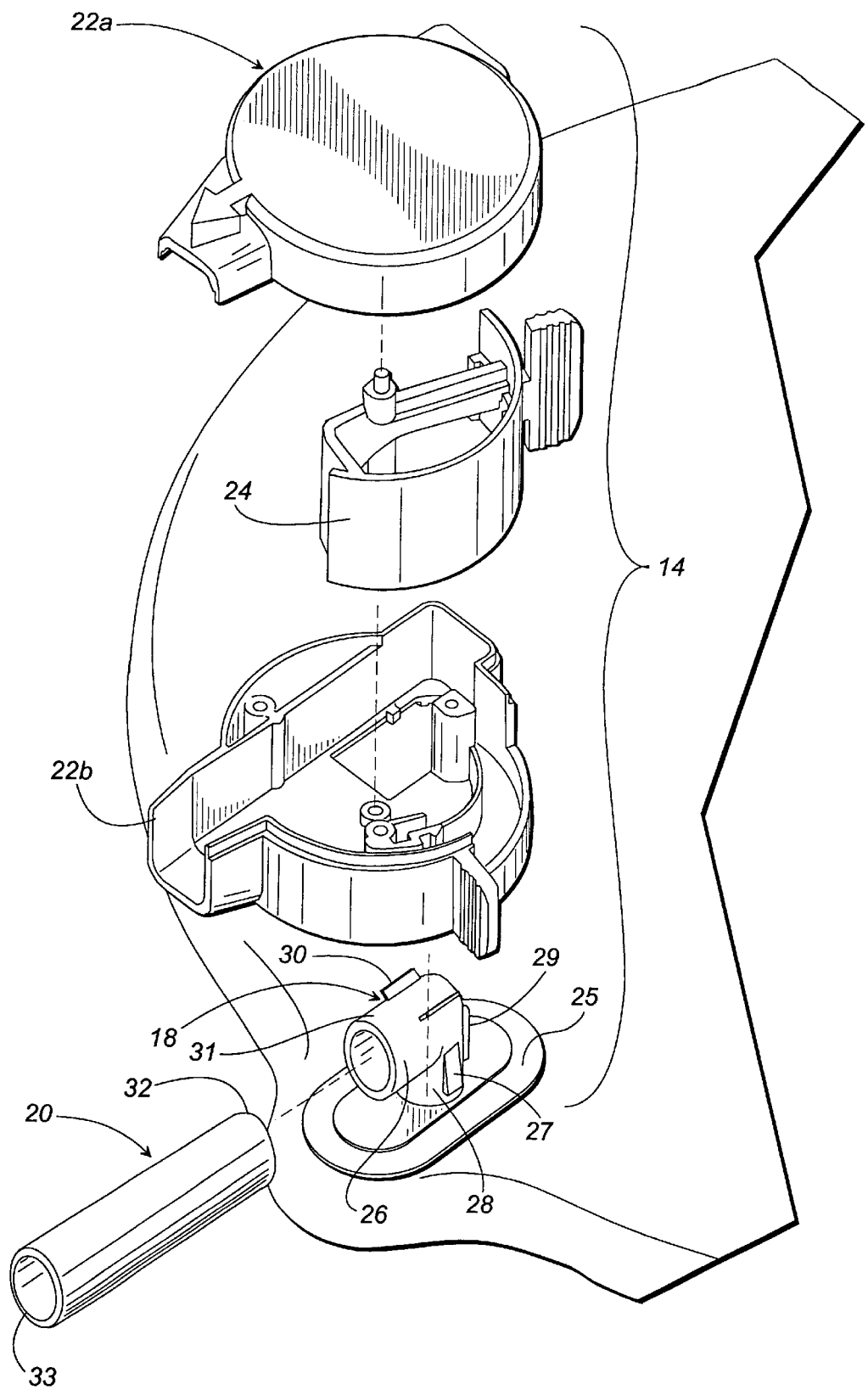
FIG. 2 is an exploded view of the drain assembly of the urine collection container of FIG. 1.

Referring now to FIG. 2, the drain assembly 14 comprises an outlet port 18, an outlet tube 20, a housing 22 consisting of a front housing 22a and a rear housing 22b, and a switch or valve member 24. Each of these elements will now be discussed in more detail.

With further reference to FIG. 2, the outlet port 18 is a molded plastic component which is welded to the lower portion of the bag 12 overlying a hole (not shown) in the front face of the bag. The outlet port 18 has a base 25 which is mounted to the front face of the bag 12. An L-shaped duct or elbow 26 projects forward from the base 25 and then downward. An opening is formed through the base 25 of the outlet port 18 and extends the length of the elbow 26. Ears 27 are formed along the lateral sides of the forward projecting leg 28 of the elbow 26, the rear edges of the ears 27 being spaced apart from the base 25 of the outlet port 18. Upward projecting ridges 29 are formed along the upper surface of the forward projecting leg 28 of the elbow 26. Vertical stops 30 are formed on the downward extending leg 31 of the elbow 26. The lower edge of each stop 30 is generally aligned with the lower edge of the forward projecting leg 28 of the elbow 26.

The outlet tube 20 is a short length of flexible, resilient tubing which has an inner diameter which is slightly smaller than the outer diameter of the lower end of the elbow 26 of the outlet port 18. The outlet tube 20 has an upper end 32 and a lower end 33. The upper end 32 of the outlet tube 20 is stretched over the lower end of the elbow 26 and is held in place by a friction fit. The outlet tube 20 is thus in fluid communication with the interior of the bag 12 by way of the outlet port 18.

Referring now to FIG. 3, the rear housing 22b has a generally circular back panel 34 and an upstanding peripheral side wall 35. The back panel 34 of the rear housing 22b has an opening 36 for receiving the elbow 26 of the outlet port 18. The thickness of the back panel 34 around the periphery of the opening 36 corresponds to the spacing between the ears 27 and the base 25 of the outlet port 18. Upward extending notches 37 are formed in the upper periphery of the opening 36. A bearing 38 consisting of upstanding cylindrical walls is formed in the center of the back panel 34. A slot 39 is formed in the side wall 35 of the rear housing 22b extending from approximately the twelve o'clock position to the three o'clock position, as viewed from the front. A finger tab 40 extends radially outward from the side wall 35 adjacent the lower end of the slot 39.

An outlet 41 is formed in the side wall 35 at the lower end of the rear housing 22b. A generally vertical, upstanding stop 42 is located on the left side of the interior of the rear housing 22b. A pair of upstanding ribs 43, 44 project upward from the back panel 34 of the rear housing 22b adjacent the side wall 35 at approximately the twelve and three o'clock positions, respectively. An arcuate wall 45 extends between the upstanding ribs 43, 44, in spaced-apart relation to the side wall 35.

Referring now to FIG. 4, the switch 24 comprises a spindle 46. A radial spoke 48 extends from the spindle 46 to an arcuate wall 50. The arcuate wall 50 proscribes a path defined by a portion of a circle having the spindle 46 as its center. The lower portion of the arcuate wall 50 serves as a shield 51, as will be further described below. A finger-receiving tab 52 extends outward from the upper end of the arcuate wall 50. An L-shaped arm 53 extends downward from the spindle 46 to the lower end of the arcuate wall 50. The outer edge of the angle of the L-shaped arm 53 constitutes a closure element 54. Hooks 56, 58 are formed on the inner surface of the arcuate wall 50 on the upper and lower sides, respectively, of the radial spoke 48.

Assembly of the drain assembly 14 will now be described. The base 25 of the outlet port 18 is RF welded or otherwise suitably attached to the front wall of the bag 12. The upper end 32 of the outlet tube 20, optionally lubricated with isopropyl alcohol, is slipped over the lower end of the elbow 26 of the outlet port 18. The outlet tube 20 is advanced upward until the upper end 32 of the outlet tube confronts the vertical stops 30 on the downward extending leg 31 of the elbow 26. The outlet tube 20 is held in place on the elbow 26 of the outlet port 18 by a friction fit.

A drain subassembly, consisting of the front and rear housings 22a, 22b and the switch 24, is now assembled. The switch 24 is installed by inserting the rearward end of the spindle 46 into the cooperating bearing 38 in the rear housing 22b. The finger-receiving tab 52 of the switch 24 extends through the slot 39 in the side wall 35 of the rear housing 22b. The design of the switch 24 is such that it cannot be inadvertently assembled into the housing 22 backward, for if the finger-receiving tab 52 is not received through the slot 39, the tab will interfere with the fit of the front and rear housings 22a, 22b. The front housing 22a is then sonically welded onto the rear housing 22b. The forward end of the spindle 46 is rotatably supported within a cooperating bearing (not shown, but corresponding generally to the bearing 38 on the rear housing 22b) on the interior surface of the front wall of the front housing 22a.

The drain subassembly is now assembled onto the outlet port 18 as follows. The lower end 33 of the outlet tube 20 is received through the opening 36 in the back panel 34 of the rear housing 22b. The drain subassembly is positioned over the outlet port 18 with the upward projecting ridges 29 on the upper surface of the forward projecting leg 28 of the elbow 26 being received within the notches 37 in the upper periphery of the opening 36 in the back panel 34 of the rear housing 22b. A portion of the back panel 34 of the rear housing 22b adjacent the opening 36 snaps behind the ears 27 on the lateral edges of the elbow 26 of the outlet port 18 to retain the drain subassembly on the outlet port. With the drain subassembly thus assembled onto the outlet port 18, the lower end 33 of the outlet tube 20 is located above the outlet 41 at the lower end of the rear housing 22b.

With the drain assembly 14 thus assembled, the arcuate wall 45 in the interior of the housing 22 prevents objects from falling into the slot 39 and visually screens the inner workings of the drain assembly when someone looks through the slot 39.

Figure 5:
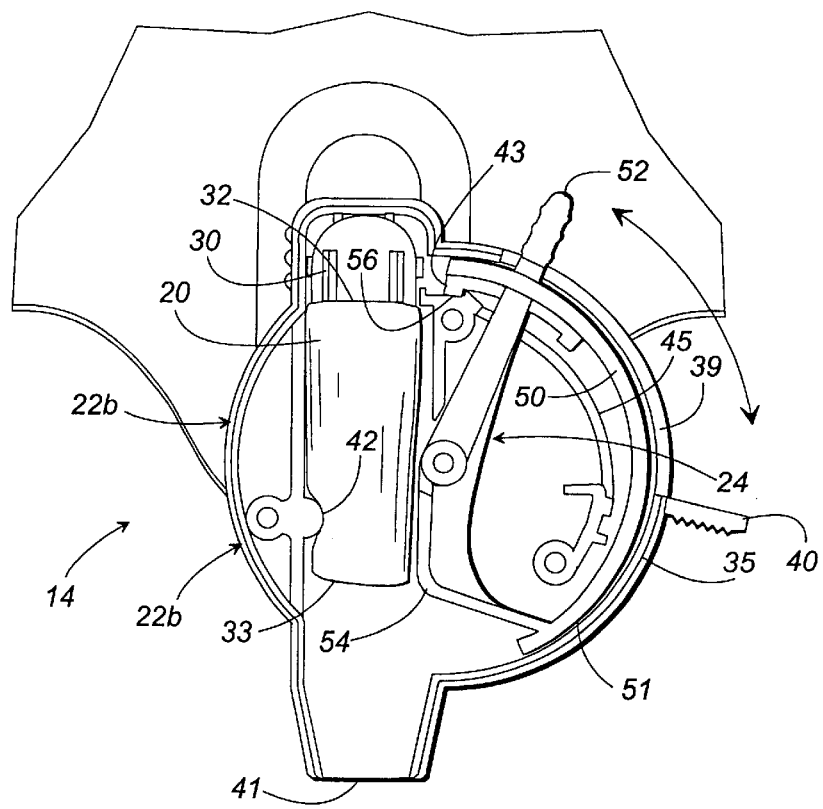
FIG. 5 is a front view of the drain assembly of FIG. 2 with front housing removed to show interior detail, with the drain assembly in its open position.

Operation of drain assembly 14 will now be discussed with reference to FIGS. 5–7. Referring first to FIG. 5, the drain assembly 10 is in its "open" state. The switch 24 has been rotated counterclockwise such that the tab 52 of the switch is at the upper end of the slot 39 in the side wall 35 of the rear housing 22b. In this position the closure element 54 exerts little or no compressive force against the outlet tube 20. The upper hook 56 on the inner surface of the arcuate wall 50 of the switch 24 engages the rib 43 extending upward from the back panel 34 of the rear housing 22b to retain the switch in the "open" position. This latch mechanism for holding the switch 24 in the "open" position is desirable from the perspective of the operator, so that the bag can be drained without the operator having to be present to hold the switch open. With the switch in this position, the shield 51 of the switch is rotated away from the outlet 41 at the lower end of the housing 22. As can be seen in FIG. 7, when the switch 24 is in the open position (solid lines), the tab 52 is aligned with a mark 70 on the face of the front housing 22a.

Figure 6:
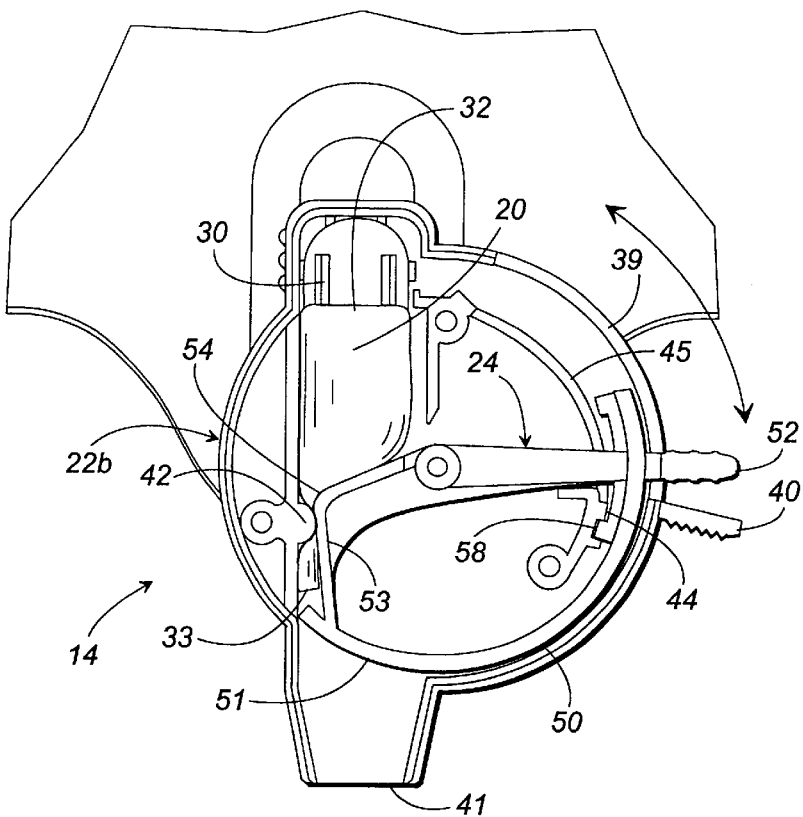
FIG. 6 is a front view of the drain assembly of FIG. 2 with front housing removed to show interior detail, with the drain assembly in its closed position.

To close the drain assembly 14, the tab 52 of the switch 24 is rotated clockwise until the tab reaches the lower end of the slot 39, as shown in FIG. 6. To facilitate rotating the switch 24, the operator places the thumb on the tab 52 of the switch and a finger on the tab 40 of the rear housing 22b and squeezes. As the switch 24 rotates, the closure member 54 comes into contact with the flexible outlet tube 20 and compresses it against the stop 42, clamping off the lumen of the tube and preventing fluid flow. The lower hook 58 on the inner surface of the arcuate wall 50 of the switch 24 engages the rib 44 on the rear housing 22b to retain the switch in the closed position. As can be seen in FIG. 7, when the switch 24 is in the closed position (phantom lines), the tab 52 is aligned with a mark 72 on the face of the front housing 22a.

As can further be seen in FIG. 6, as the switch 24 is closed, the shield 51 of the switch rotates into position over the outlet 41 at the lower end of the housing 22. With the shield 51 thus covering the outlet 41, the possibility is eliminated of an operator's finger or other foreign object coming into contact with the lower end of the outlet tube 20 and causing contamination. The shield 51 also provides the aesthetic benefit that the inner workings of the drain assembly 14 are concealed from view.

To open the drain assembly 14 to drain the bag or to collect a specimen for analysis, the tab 52 of the switch 24 is rotated counterclockwise. As the switch 24 rotates, the shield 51 rotates upward, uncovering the outlet 41 at the lower end of the housing. Further rotation of the switch 24 causes the closure member 54 to disengage from the outlet tube 20. The resiliency of the outlet tube 20 and the fluid pressure exerted by the contents of the bag 12 cause the tube to open, and fluid is discharged from the lower end 32 of the outlet tube 20 and through the outlet 41 at the lower end of the housing. If it is desired to maintain the drain assembly 14 in the open position, rotation of the switch 24 to its full counterclockwise position will bring the hook 56 on the upper side of the spoke 48 into engagement with the upper rib 43, thereby locking the switch in the open position.

It will be appreciated that the outlet 41 at the discharge end of the housing 22 is shaped to control the direction in which fluid is discharged from the drain assembly 14. The outlet 41 also provides a visual cue to the operator where the discharge will be directed.

The switch 24 is designed so that as it is closed, the flexible outlet tube 20 is compressed beyond the point needed to occlude the lumen of the tube. The reason for this design is that as the switch 24 is opened, the switch can be rotated a short distance with the tube still remaining closed. This rotation gives the shield 51 the opportunity to rotate away from the outlet 41, so that by the time the outlet tube 20 opens and fluid begins to be discharged, the shield is out of the way.

A feature of the disclosed embodiment is that the user receives three distinct types of confirmation—visual, tactile, and audible—that the switch is locked in the "open" or "closed" position. When the switch 24 is fully open or closed, the operator receives visual confirmation, in that the tab 52 is aligned with a mark 70 or 72 on the face of the front housing 22a. In addition, when a hook 56 or 58 engages the corresponding rib 43 or 44, it snaps into place, causing vibrations which can be felt by the operator. Finally, the snapping action creates an audible "click" sound, which can be heard by the operator. The tactile and audible confirmations can be very advantageous in a hospital environment, where the operator may be working in darkened or dimly lit rooms, or where the bag may be hung well below eye level such that the operator cannot easily see the visual indicators.

Another feature of the disclosed embodiment is that the switch 24 compresses the outlet tube 20 along a length of the tube, rather than at a single point. As can be seen in FIG. 6, when the switch 24 is in its closed position, not only the closure element 54 but also the lower end of the L-shaped arm 53 bears against the outlet tube 20, compressing the tubing all the way to its lower end. This action squeezes out any residual drops of urine which may be clinging to the inner walls of the outlet tube 20 at its lower end, preventing the residual urine from dripping out at a later, inopportune time.

Still another feature of the disclosed embodiment is that the drain assembly 14 is designed to avoid pinching or tearing protective gloves of the operator. For example, edges of the device are rounded. Also, there is a spacing between the tab 52 of the switch 24 and the finger tab 40 on the housing 22, even when the switch is fully closed, so that a glove will not be pinched between the tabs. In addition, the latch mechanisms for maintaining the drain assembly 14 in the fully open or fully closed positions are concealed within the housing 22 so as not to present a pinch hazard.

As a practical matter, the housing 22 must be formed of at least two mating members to permit the switch 24 to be installed within the housing. However, while the housing 22 of the disclosed embodiment consists of front and rear housing portions 22a, 22b, it will be appreciated that other mating housing portion arrangements can be utilized. For example, the housing could be split into two portions along any plane which permits the spindle 46 of the switch 24 to be rotatably mounted within the housing, e.g., top and bottom housing portions, or left and right housing portions. As another alternative, the housing 22 could be comprised of more than two portions, e.g., a front housing portion, a rear housing portion, and a cylindrical side wall portion to which the front and rear housing portions are mounted.

In addition, while the switch 24 of the disclosed embodiment comprises a tab 52 which extends through a slot 39 in the side wall 41 of the housing 22, it will be understood that other means for facilitating rotational movement of the switch from outside the housing can be used. For example, the spindle 46 of the switch 24 could extend through the front wall of the housing and have a knob or crank mounted at its forward end, whereby a user could grasp the knob or crank and turn it to operate the switch to open or close the drain assembly.

The present invention provides a number of advantages. The housing 22 can be grasped with one hand while a finger of that hand moves the tab 52 to open or to close the drain, thereby permitting one-handed operation. Further, since the outlet tube 20 is essentially fixed with respect to the housing 22, the user can control the direction of fluid discharge as they hold the housing. Also, because the lower end 33 of the outlet tube 20 is recessed within the outlet 41 at the lower end of the housing 22, the possibility of direct contact by the user with the outlet tube is minimized, thereby avoiding contamination. And because the action of the tab 52 sliding within the slot 39 in the side wall of the housing is intuitive, ease of operation is enhanced.

It will also be appreciated that the first hook 56 on the switch 24 and first the rib 43 on the housing 22 form a first cooperating latch means for retaining the switch in its "open" position, and the second hook 58 on the switch 24 and the second rib 44 on the housing 22 form a second cooperating latch means for retaining the switch in its "closed" position. While the disclosed embodiment utilizes hooks 56, 58 on the switch 24 which engage ribs 43, 44 on the housing 22 to retain the switch in an "open" or "closed" position, other latch means may readily be substituted. For example, the hooks can be formed on the housing to engage ribs on the switch, or hooks can be formed on both the housing and the switch which mutually engage to retain the switch in the desired position. Or an element on one of the switch or housing can frictionally engage a cooperating element on the other of the switch or housing to retain the switch in the desired position. Other latch means will be readily apparent to those skilled in the art.

Finally, it will be understood that the preferred embodiment has been disclosed by way of example, and that other modifications may occur to those skilled in the art without departing from the scope and spirit of the appended claims.

What is claimed is:

1. An apparatus comprising:
    a fluid collection container;
    a front housing portion;
    a rear housing portion mounted to said front housing portion in stationary relation thereto to form a housing, said housing defining a cavity therewithin, said housing having an opening in a lower portion thereof, and said housing being fixedly mounted to said fluid collection container;
    a stop located within said cavity and being fixed relative to said housing;
    a switch mounted within said cavity for rotary movement relative to said housing, said switch having a closure member formed thereon; and
    a flexible, resilient tube in fluid communication with the interior of said fluid collection container, said tube having a portion disposed within said cavity and extending between said stop and said closure member of said switch, and said tube being configured to discharge fluid from a lower end thereof through said opening in said lower portion of said housing;
    said stop and said closure member being configured such that rotating said switch causes said portion of said tube to be compressed between said stop and said closure member to prevent fluid flow through said tube;
    whereby rotating said switch to cause said closure member to rotate away from said stop permits said tube to open, thereby permitting fluid flow through said tube and to be discharged through said opening in said lower portion of said housing.

2. The apparatus of claim 1, wherein said lower end of said tube is recessed within said housing, thereby minimizing the possibility of contamination resulting from direct contact by a user with said tube.

3. The apparatus of claim 1, wherein said housing further defines a slot therethrough, and further comprising a tab extending through said slot and operatively associated with said switch such that sliding said tab within said slot causes said switch to rotate.

4. The apparatus of claim 1, wherein said switch includes a spindle having first and second ends, wherein said housing comprises a mutually opposed pair of bearings, and wherein said switch is mounted within said cavity for rotary movement relative to said housing by said first and second ends of said spindle rotatably engaging said bearings.

5. The apparatus of claim 1, further comprising a latch means for retaining said switch in a closed position.

6. The drain assembly of claim 5, further comprising a latch means for retaining said switch in said open position.

7. The apparatus of claim 5, wherein rotating said closure member causes said portion of said tube to be compressed between said stop and said closure member to prevent fluid flow through said tube before said latch means for retaining said switch in a closed position engages said switch such that said tube is compressed beyond a point needed to occlude said tube.

8. The apparatus of claim 7, wherein said closure member further comprises a shield member operatively associated therewith, said shield member being operative to close said opening in said lower end of said housing when said latch means for retaining said switch in a closed position engages said switch.

9. The apparatus of claim 8, wherein rotating said switch closure member causes said portion of said tube to be compressed between said stop and said closure member to prevent fluid flow through said tube before said shield member is operative to close said opening in said lower end of said housing.

10. The apparatus of claim 8, wherein when said switch is rotated to cause said closure member to rotate away from said stop, said shield uncovers said opening before said closure member clears said stop by a distance sufficient to permit said tube to open.

11. The apparatus of claim 8, wherein said shield member is connected to said switch closure member and rotates therewith.

12. The apparatus of claim 1, further comprising a latch means for retaining said switch in said open position.

13. The apparatus of claim 1, wherein said housing comprises a spout formed in a lower portion thereof, wherein said opening in said lower end of said housing comprises said opening being formed in a lower end of said spout, and wherein said flexible, resilient tube is configured to discharge fluid through said spout.

14. The apparatus of claim 1, further comprising an upstanding wall formed within said cavity of said housing in generally parallel relation and adjacent to said tube, said stop comprising a projection formed on said upstanding wall and extending toward said tube.

15. The apparatus of claim 14, wherein said stop is substantially semicircular.

16. The apparatus of claim 14, wherein said stop is disposed on said upstanding wall at a location spaced upward from said lower end of said tube.

17. The apparatus of claim 14, wherein said switch further comprises a leg extending from said closure member, said switch being configured such that when said switch is rotated to compress said tube between said stop and said closure member to prevent fluid flow through said tube, further rotation of said switch causes said leg to compress against said upstanding wall a portion of said tube below said portion extending between said stop and said closure member so as to force any fluid within said portion of said tube below said portion extending between said stop and said closure member out said lower end of said tube.

18. An apparatus comprising:
   a fluid collection container;
   a front housing portion;
   a rear housing portion mounted to said front housing portion in stationary relation thereto to form a housing, said housing defining a cavity therewithin, said housing having an opening in a lower portion thereof, and said housing being attached to said fluid collection container;
   a stop located within said cavity and being fixed relative to said housing;
   a switch mounted within said cavity for rotary movement relative to said housing, said switch having a closure member formed thereon; and
   a flexible, resilient tube in fluid communication with the interior of said fluid collection container, said tube having a portion disposed within said cavity and extending between said stop and said closure member of said switch, and said tube being configured to discharge fluid from a lower end thereof through said opening in said lower portion of said housing, and said lower end of said tube is recessed within said housing, thereby minimizing the possibility of contamination resulting from direct contact by a user with the lower end of said tube;
   said stop and said closure member being configured such that rotating said switch causes said portion of said tube to be compressed between said stop and said closure member to prevent fluid flow through said tube;
   whereby rotating said switch to cause said closure member to rotate away from said stop permits said tube to open, thereby permitting fluid flow through said tube and to be discharged through said opening in said lower portion of said housing.

19. The apparatus of claim 18, wherein said housing further defines a slot therethrough, and further comprising a tab extending through said slot and operatively associated with said switch such that sliding said tab within said slot causes said switch to rotate.

20. The apparatus of claim 18, wherein said switch includes a spindle having first and second ends, wherein said housing comprises a mutually opposed pair of bearings, and wherein said switch is mounted within said cavity for rotary movement relative to said housing by said first and second ends of said spindle rotatably engaging said bearings.

21. The apparatus of claim 18, further comprising a latch means for retaining said switch in a closed position.

22. The apparatus of claim 21, wherein rotating said closure member causes said portion of said tube to be compressed between said stop and said closure member to prevent fluid flow through said tube before said latch means for retaining said switch in a closed position engages said switch such that said tube is compressed beyond a point needed to occlude said tube.

23. The apparatus of claim 22, wherein said closure member further comprises a shield member operatively associated therewith, said shield member being operative to close said opening in said lower end of said housing when said latch means for retaining said switch in a closed position engages said switch.

24. The apparatus of claim 23, wherein rotating said switch closure member causes said portion of said tube to be compressed between said stop and said closure member to prevent fluid flow through said tube before said shield member is operative to close said opening in said lower end of said housing.

25. The apparatus of claim 23, wherein when said switch is rotated to cause said closure member to rotate away from said stop, said shield uncovers said opening before said closure member clears said stop by a distance sufficient to permit said tube to open.

26. The apparatus of claim 23, wherein said shield member is connected to said switch closure member and rotates therewith.

27. The apparatus of claim 18, further comprising a latch means for retaining said switch in said open position.

28. The drain assembly of claim 18, further comprising a latch means for retaining said switch in said open position.

29. The apparatus of claim 18, wherein said housing comprises a spout formed in a lower portion thereof, wherein said opening in said lower end of said housing comprises said opening being formed in a lower end of said spout, and wherein said flexible, resilient tube is configured to discharge fluid through said spout.

30. The apparatus of claim 18, further comprising an upstanding wall formed within said cavity of said housing in generally parallel relation and adjacent to said tube, said stop comprising a projection formed on said upstanding wall and extending toward said tube.

31. The apparatus of claim 30, wherein said stop is substantially semicircular.

32. The apparatus of claim 30, wherein said stop is disposed on said upstanding wall at a location spaced upward from said lower end of said tube.

33. The apparatus of claim 30, wherein said switch further comprises a leg extending from said closure member, said switch being configured such that when said switch is rotated to compress said tube between said stop and said closure member to prevent fluid flow through said tube, further rotation of said switch causes said leg to compress against said upstanding wall a portion of said tube below said portion extending between said stop and said closure member so as to force any fluid within said portion of said tube below said portion extending between said stop and said closure member out said lower end of said tube.

* * * * *